US011622583B2

(12) United States Patent
Newton

(10) Patent No.: US 11,622,583 B2
(45) Date of Patent: Apr. 11, 2023

(54) PERSONAL VAPORIZER WITH BREACH DETECTION

(71) Applicant: Kyle D. Newton, Colleyville, TX (US)

(72) Inventor: Kyle D. Newton, Colleyville, TX (US)

(*) Notice: Subject to any disclaimer, the term of this patent is extended or adjusted under 35 U.S.C. 154(b) by 421 days.

(21) Appl. No.: 16/992,365

(22) Filed: Aug. 13, 2020

(65) Prior Publication Data

US 2022/0046996 A1  Feb. 17, 2022

(51) Int. Cl.
| | | |
|---|---|---|
| A24F 13/00 | (2006.01) | |
| A24F 17/00 | (2006.01) | |
| A24F 25/00 | (2006.01) | |
| A24F 40/53 | (2020.01) | |
| G01N 27/24 | (2006.01) | |
| G01N 27/20 | (2006.01) | |
| G01N 27/22 | (2006.01) | |
| A24F 40/42 | (2020.01) | |
| A24F 40/51 | (2020.01) | |
| A61M 15/06 | (2006.01) | |
| A61M 11/04 | (2006.01) | |

(Continued)

(52) U.S. Cl.
CPC ............. *A24F 40/53* (2020.01); *A24F 40/10* (2020.01); *A24F 40/42* (2020.01); *A24F 40/51* (2020.01); *A61M 11/041* (2013.01); *A61M 15/06* (2013.01); *G01N 27/20* (2013.01); *G01N 27/228* (2013.01); *G01N 27/24* (2013.01); *A61M 2205/3327* (2013.01); *A61M 2205/8206* (2013.01); *A61M 2209/02* (2013.01); *H05B 3/0014* (2013.01)

(58) Field of Classification Search
CPC .......... A24F 40/10; A24F 40/42; A24F 40/51; A24F 40/53; A61M 11/041; A61M 11/042; A61M 15/06; A61M 2205/0233; A61M 2205/0238; A61M 2205/18; A61M 2205/276; A61M 2205/3317; A61M 2205/3327; A61M 2205/581; A61M 2205/583; A61M 2205/8206; A61M 2209/02; G01N 27/20; G01N 27/228; G01N 27/24; H05B 2203/014; H05B 2203/021; H05B 2203/022; H05B 3/0014; H05B 3/04; H05B 3/145; H05B 3/42
See application file for complete search history.

(56) References Cited

U.S. PATENT DOCUMENTS 5,665,262 A * 9/1997 Hajaligol ................ A24F 40/46
                                                    131/194
8,746,240 B2    6/2014 Terry et al.
(Continued)

FOREIGN PATENT DOCUMENTS

WO    WO-2014130002 A2 *  8/2014 ........... B41J 2/14129

*Primary Examiner* — Hae Moon Hyeon
*Assistant Examiner* — Thang H Nguyen
(74) *Attorney, Agent, or Firm* — Fish & Richardson P.C.

(57) ABSTRACT

The present disclosure describes a personal vaporizer which can detect whether or not a cartridge of the personal vaporizer has been breached. The cartridge includes a conductive shell. The conductive shell can include two or more conductors which are electrically isolated from each-other. Prior to operation, the personal vaporizer can use the two or more conductors to assess whether or not an outer shell of the cartridge has been breached. In some implementations, if it is determined that the cartridge has been breached, the personal vaporizer can shut down, or otherwise fail to operate normally.

20 Claims, 4 Drawing Sheets

(51) Int. Cl.
*A24F 40/10* (2020.01)
*H05B 3/00* (2006.01)

(56) References Cited

U.S. PATENT DOCUMENTS

| | | |
|---|---|---|
| 8,910,630 B2 | 12/2014 | Todd |
| 9,999,250 B2 * | 6/2018 | Minskoff ................. H05B 3/12 |
| 10,099,916 B2 | 10/2018 | Murison et al. |
| 2016/0021930 A1 | 1/2016 | Minskoff et al. |
| 2016/0150828 A1 | 6/2016 | Goldstein et al. |
| 2016/0183596 A1 * | 6/2016 | Rado ....................... F22B 1/284 |
| | | 392/404 |
| 2016/0211693 A1 | 7/2016 | Stevens et al. |
| 2017/0258137 A1 * | 9/2017 | Smith ..................... A24F 40/53 |
| 2018/0043114 A1 * | 2/2018 | Bowen ................. A61M 11/042 |
| 2018/0117268 A1 * | 5/2018 | Selby ................... A61M 15/06 |

* cited by examiner

PERSONAL VAPORIZER WITH BREACH DETECTION

BACKGROUND

Personal vaporizers provide an alternative to smoking techniques which involve combustion of organic matter and inhalation of the vapor. Instead vaporizers atomize a substance (e.g., a nicotine substance or cannabis substance) using a heating element to simulate the combustion found in traditional cigarettes. Personal vaporizers often use removable/replaceable cartridges containing a substance for atomization. Unauthorized or uncontrolled breach of the cartridge or contamination of the substance in the cartridge can be unsafe for the user of the personal vaporizer.

SUMMARY

The present disclosure involves systems, methods, and an apparatus for identifying a breach or penetration of a reservoir of a personal vaporizer. One example implementation includes a personal vaporizer cartridge that has a housing which includes a shell and a base, the housing configured to couple with a power supply portion a personal vaporizer. The shell includes a first conductive layer, a second conductive layer, and an insulation layer between the first and the second conductive layers. The insulation layer electrically isolates the first conductive layer from the second conductive layer. The first and second conductive layers are configured to be connected to a testing circuit, the testing circuit measuring at least one electrical parameter associated with the shell. The personal vaporizer cartridge includes a reservoir enclosed by the housing and configured to contain a substance to be vaporized, and a wick configured to transport the substance from the reservoir to an atomization chamber.

Implementations can optionally include one or more of the following features.

In some instances, the atomization chamber is configured to atomize the substance to be vaporized and generate an aerosol. The atomization chamber can include a heating element and an air inlet to allow airflow through the atomization chamber into a chimney, the chimney forming a channel between the atomization chamber and an external space.

In some instances, the insulation layer is a dielectric material, and a predetermined capacitance is present between the first conductive layer and the second conductive layer. The testing circuit can be configured to measure a capacitance between the first conductive layer and the second conductive layer and compare the measured capacitance with the predetermined capacitance.

In some instances, the first conductive layer is electrically connected to a voltage reference on the cartridge, and the second conductive layer further includes a conductive tab that penetrates the base and is configured to form an electric connection with the testing circuit on the power supply portion of the personal vaporizer.

In some instances, an outer surface of the second conductive layer is enclosed with a paper, plastic, or printed material.

In some instances, the electrical parameter associated with the shell is a continuity between the first conductive layer and the second conductive layer.

Another example implementation includes a method for assessing the condition of a cartridge of a personal vaporizer, the method including: upon the cartridge being coupled with a power supply portion of the personal vaporizer, analyzing an electrical characteristic between a first conductive layer and a second conductive layer of a shell which encloses at least a portion of a fluid reservoir of the cartridge. In response to analyzing the electrical characteristic, determining that the shell has been breached.

In some instances, analyzing the electrical characteristic includes performing a continuity check, and it is determined that the shell has been breached when there is continuity between the first conductive layer and the second conductive layer.

In some instances, analyzing the electrical characteristic includes measuring a capacitance, and it is determined that the shell has been breached when capacitance is below a predetermined threshold.

In some instances, in response to determining the cartridge has been breached an action is performed. The action can include interrupting a signal between the power supply portion of the personal vaporizer and a heating element. The action can include electrically overloading at least one component in the cartridge. The action can include providing an indication that the cartridge has been breached.

Another example implementation includes a personal vaporizer configured to atomize a substance and generate an aerosol, the vaporizer including: a power supply portion; a cartridge portion that is configured to be coupled to the power supply portion, including a shell that has a first conductive layer, a second conductive layer, and an insulation layer between the first and second conductive layers that electrically isolates the first conductive layer from the second conductive layer; a testing circuit that is configured to measure at least one electrical parameter associated with the shell; and a battery.

In some instances, the testing circuit is within the power supply portion of the personal vaporizer.

In some instances, the first conductive layer is electrically connected to a voltage reference on the cartridge, and the second conductive layer includes a conductive tab that penetrates a base of the cartridge, and is configured to form an electric connection with the testing circuit on the power supply portion of the vaporizer.

In some instances, the testing circuit is within the cartridge portion of the personal vaporizer.

In some instances the electrical parameter associated with the shell includes at least one of electrical continuity, a capacitance between the first conductive layer and the second conductive layer, a resistance between the first conductive layer and the second conductive layer, or a combination thereof.

In some instances, an outer surface of the second conductive layer is enclosed with a paper, plastic, or printed material.

The details of these and other aspects and embodiments of the present disclosure are set forth in the accompanying drawings and the description below. Other features, objects, and advantages of the disclosure will be apparent from the description and drawings, and from the claims.

DETAILED DESCRIPTION

Figure 1:
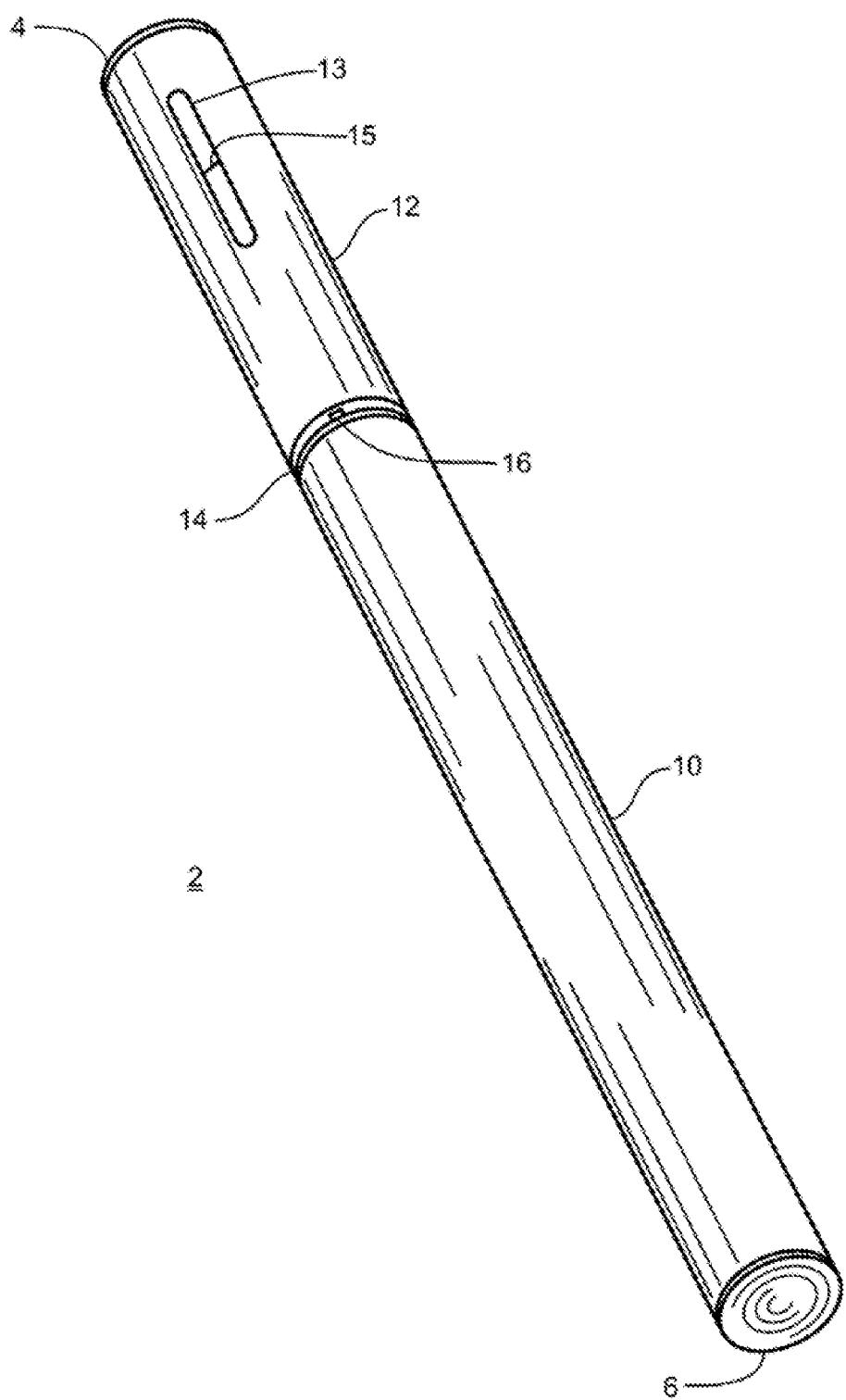
FIG. 1 depicts a perspective view of an example implementation of a personal vaporizer.

This disclosure describes a personal vaporizer such as an electronic cigarette, a vape pen, vape kits, e-cig, or e-hookah, electronic nicotine delivery system which can detect whether or not a cartridge of the personal vaporizer has been breached. In some implementations, personal vaporizers use removable or disposable cartridges to provide a substance to be vaporized for inhalation. Example substances can include, but are not limited to tobacco, cannabis, opium, amphetamines, or other recreational or medicinal substances. In some cases, these substances are controlled (e.g., by the manufacturer or regulated based on legal requirements) and thus it is desirable to detect any breach of the cartridge once it has been filled with the substance. A breach detection system which permits detection of breaches in the cartridge can prevent malicious or inadvertent altering of the substance before it is consumed by the user, either by an intervening party, or the user itself. As described herein, a conductive shell can enclose, or partially enclose a reservoir containing the substance, and permit an integrity check to be performed on the cartridge prior to use.

The conductive shell can include two or more conductors which are electrically isolated from each-other. Prior to operation, the personal vaporizer can use the two or more conductors to assess whether or not an outer shell of the cartridge has been breached. In some implementations, if it is determined that the cartridge has been breached, the personal vaporizer can shut down, or otherwise fail to operate normally (e.g., indicate an error and refuse to provide a voltage to a heating element to atomize the substance in the cartridge).

The conductive shell can include an inner and an outer conductor, separated by a layer of insulation. The outer conductor can be a material which is readily plastically deformed if a force is applied to it. For example, if a needle is used to puncture the cartridge (e.g., to extract the substance or to add unapproved substances) the outer conductor can plastically deform, bending inward and making contact with the inner conductor, and therefore electrically connecting the inner and outer conductors. In some implementations, if the substance within the reservoir is conductive, leaking substance can complete an electrical connection between the inner and outer conductors if the inner conductor is punctured. When the cartridge is coupled with a power supply or controller portions of the personal vaporizer, a continuity check can be performed between the inner and outer conductor. If a conductive path exists between the inner and outer conductors, then it is likely the conductive shell has been punctured or penetrated in some way.

In some implementations, a conductive path between the inner and outer conductors is not necessary for detecting a breach or penetration. For example, the layer of insulation can be a dielectric material, and the conductive shell can have a predetermined capacitance between the inner and outer conductors. Prior to use, a capacitance across the inner and outer conductors can be measured. A significant deviation from the predetermined capacitance can indicate a breach in the conductive shell (e.g., dents, punctures, scratches, and/or other deformities).

Turning to the illustrated example implementation, FIG. 1 is a perspective view of a personal vaporizer. While illustrated in the form factor of an electronic cigarette, the concepts herein could be applied to other types of personal vaporizers such as e-hookahs, vape kits, vape pens, etc. The example personal vaporizer 2 includes a housing having a first elongated portion 10 and a second elongated portion 12. The second elongated portion 12, also referred to as the "cartridge" in certain illustrative implementations, includes a mouthpiece end 4, which has an aerosol outlet (depicted in FIG. 3) for drawing air through the cartridge 12. The first elongated portion 10 and the second elongated portion 12 are seperably joined together with a mechanical coupler 14. One or more air inlet vents 16 are provided about the mechanical coupler 14 for allowing airflow into the cartridge 12 when the user draws air through the personal vaporizer 2. The first elongated portion 10 includes a tip end 6, which in the illustrative implementation, is fabricated from a translucent material enabling the transmission of light therethrough. Within the second elongated portion 12 is disposed a liquid reservoir (not fully shown). In some implementations, the liquid reservoir includes a clear or translucent window 13 to the exterior of the cartridge 12 for visually determining the liquid level 15 within the liquid reservoir.

Figure 2:
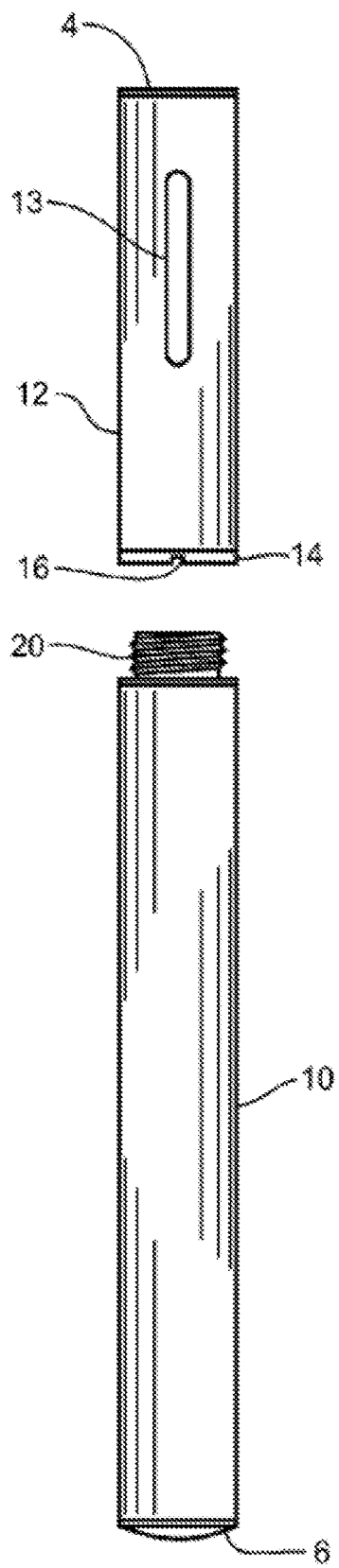
FIG. 2 depicts a side view of an example personal vaporizer with a removable cartridge removed.

FIG. 2 depicts a side view drawing, respectively, of a cartridge 12 and a power supply portion 10 of a personal vaporizer 2 according to an illustrative embodiment of the present invention. The mechanical coupler 14 can have two parts, one that is part of the cartridge 12 and one that is part of the power supply portion, e.g., one part being female and configured to receive the other, male, part. For example, the mechanical coupler can be threads, a lug/channel connector, a recessed magnetic connector or other suitable means for coupling the two portions of the personal vaporizer 2. FIG. 2 shows the mechanical coupler 14 portion on the power supply portion 10 in the form of a threaded extension 20 of the housing that engages female threads of the mechanical coupler 14 portion on the cartridge 12. In some implementations (as shown below and discussed with reference to in FIG. 3), the cartridge 12 can include a threaded or male portion, which engages with female threads of the power supply portion 10. In addition, an electrical connection can also be facilitated in the connection between the mechanical coupler 14 parts. In some implementations, the mechanical coupler 14 can be a magnetic, or snap coupler in which the power supply portion 10 and the cartridge are coupled using magnetic fields, or friction. The power supply portion 10 can include one or more circuits for controlling operations of the cartridge 12. The power supply portion 10 can further include one or more circuits for testing the condition of the cartridge 12. The circuits can be analog or digital and can include, for example, a microcontroller and various sensors to enable operation of the personal vaporizer 2. In this example illustration, the cartridge 12 can thusly be installed, uninstalled, and replaced as needed. The cartridge portion contains the liquid reservoir and the window 13 provides the visual indication as to the liquid remaining.

Figure 3:
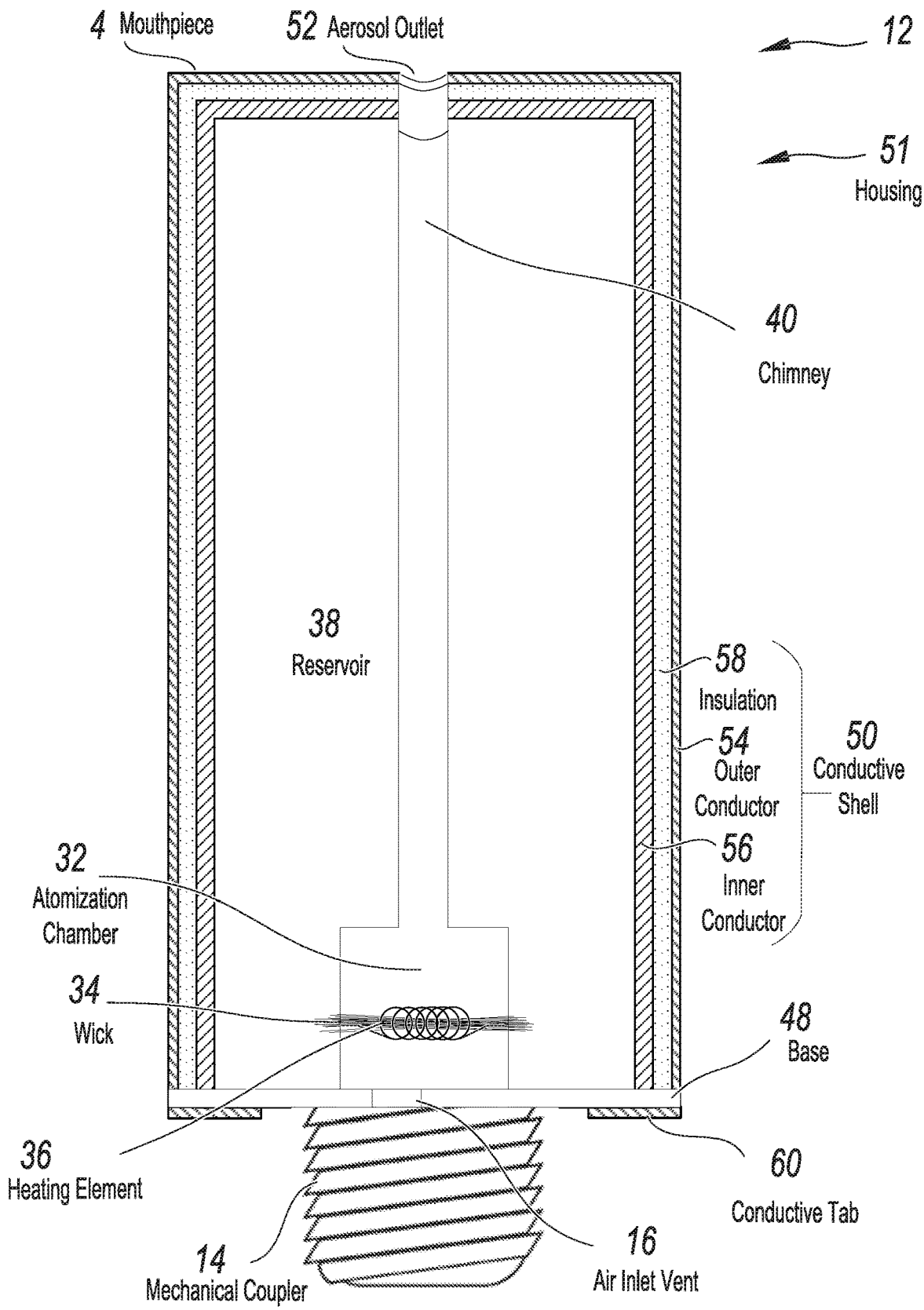
FIG. 3 illustrates a half cross-sectional view of a cartridge with a breach responsive shell.

FIG. 3 is a half cross-sectional view of an example implementation of a cartridge 12 with a breach detection capability. The cartridge 12 includes a conductive shell 50 which is made up of an outer conductor 54, inner conductor 56, an insulation layer 58 in between the two conductors, a base 48, and a mechanical coupler 14. As depicted in FIG. 3, the conductive shell 50 forms the housing 51 for the cartridge. In some implementations, the housing 51 is separate from the conductive shell 50. For example, in some implementations the conductive shell 50 is a thin film affixed to the inside of the housing 51. An atomization chamber 32 and chimney 40 are shown located within the conductive shell 50, but in other instances, the atomization chamber 32 can be located elsewhere. The chimney 40 extends from the atomization chamber 32 to an opening in the mouthpiece 4 of the cartridge. The atomization chamber can include a wick 34 and a heating element 36, while the chimney 40 can form the aerosol outlet 52 and provide a flow path from air inlet vent 16 through the cartridge 12. The atomization chamber 32 and chimney 40 define an inner wall to a reservoir 38, which is inside of the conductive shell 50 and the base 48.

The atomization chamber 32 receives a primary substance in liquid form from the reservoir 38 via the wick 34. The wick 34 can be a fibrous bundle that draws liquid via capillary action from the reservoir 38. The wick 34 extends from the primary reservoir into the atomization chamber 32. It can be formed of a suitable heat-resistant wicking material, such as aramid, fluorocarbon, sulfide, melamine, polyimide, carbon, glass fibers, or any combination thereof. The heating element 36 can be a resistive coil that generates heat when electrical current passes through it. The heating element 36 can be supplied with electrical power from the power supply portion 10 of the personal vaporizer. The heating element 36 is located proximal to the wick 34 (in the example illustrated in FIG. 3 it is wrapped around the wick 34), heats the liquid carried from the reservoir 38 by the wick 34 and atomizes the primary substance which mixes with air in the atomization chamber to form an aerosol. One or more air inlet vents 16 near the bottom of the cartridge 12 allow airflow from the air inlet vent 16, through the atomization chamber 32 and out the chimney 40.

During normal operation, a user draws a suction on the cartridge via inhaling, air enters the cartridge via the air inlet vents 16, and passes through the atomization chamber 32, where it is mixed with the primary substance which has been atomized from the wick 34 by the heating element 36 to form an aerosol. The aerosol continues up the chimney 40 and exits the cartridge 12 through the mouthpiece 4. As the primary substance on the wick 34 is depleted, more is pulled in from the reservoir 38 via capillary action along the wick 34.

The conductive shell 50 can be mounted to the base 48 and can, in some implementations, be a sealed structural component, e.g., a wall, that defines all or at least a portion of the reservoir 38. In some implementations, the conductive shell 50 is not a structural component, and merely encloses an additional structural component, e.g., a wall, that defines all or at least a portion of the reservoir 38 and/or the exterior of the cartridge 12. In some implementations, the conductive shell 50 is enclosed within the cartridge, which has a structural component defining its exterior (e.g., a plastic or aluminum external shell). The conductive shell 50 includes an inner conductor 56, an outer conductor 54, and an insulation layer 58. In some implementations, the outer conductor 54 is wrapped or coated with additional material. For example, in implementations where the cartridge is placed directly in a user's mouth, it may be desirable to coat the outer conductor in an insulated material, such as a rubberized powder-coat or other material. In some implementations, the outer conductor 54 is wrapped with a paper material that is adhered to the outside (e.g., a sticker) which can provide aesthetic graphics and a more desirable surface upon which the user can place their mouth. The outer conductor 54 can partially enclosed with a paper, plastic, or printed material, or wholly enclosed. In some implementations, wholly enclosed means the outer conductor is no longer visible, or has its outer surface fully covered by the sticker. In some implementations, the outer conductor 54 is adhered to the exterior of housing 51, or embedded withins The inner conductor 56 can be a metallic material or include a metallic material to provide a conductive path for electrons to flow. The inner conductor 56 can be, for example, copper, aluminum, steel or a steel alloy, graphite, or other suitable conductor. The inner conductor 56 can be a structural component of the cartridge or a film or screen applied to the structural component (e.g., housing 51). In some implementations, the inner conductor 56 can be a combination of the foregoing (e.g., partially structural with a screen in some portions to reduce weight. For example, in some implementations the inner conductor 56 can be a screen embedded in the side of a plastic wall which forms a liquid tight wall of the reservoir 38. In some implementations, the inner conductor 56 can provide a seal with the base 48 and is a wall that defines the reservoir 38, containing a liquid substance to be vaporized. In some implementations, the inner conductor 56 can be electrically connected to the mechanical coupler 14, or a reference ground associated with the heating element 36. In some implementations, the inner conductor 56 is electrically floating, e.g., not electrically connected to any other components of the cartridge, and is configured to come into contact with a testing circuit (e.g., test circuit 82 as described with reference to FIGS. 4A-C) when the cartridge 12 is coupled with a power supply portion of the personal vaporizer (e.g., power supply portion 10 as discussed with reference to FIG. 2.)

The outer conductor 54 can be a metallic material or include a metallic material, such as a mesh or screen which can cause an electrical connection with any other conductor it comes into contact with. In some implementations, the outer conductor 54 can be formed of a material that readily plastically deforms in response to a breach of the outer conductor 54 (e.g., blunt force, puncturing, or shear). The outer conductor 54 can be electrically connected to a circuit or, in some implementations, not electrically connected to any other portion of the cartridge 12. In FIG. 3, the outer conductor 54 is shown including one or more conductive tabs 60, which penetrate or wrap around at least a portion of the base 48 and be positioned to come into contact with a testing circuit (e.g., test circuit 82 as described with reference to FIGS. 4A-C) when the cartridge 12 is coupled using the mechanical coupler 14. Similarly to the inner conductor 56, the outer conductor 54 can be made of copper, aluminum, steel or a steel alloy, graphite or other suitable conductor. The outer conductor 54 can be a structural component, or a film applied to a structural component (e.g., housing 51). In some implementations the outer conductor 54 is a screen embedded or partially embedded in the housing 51.

An insulation layer 58 disposed between the inner conductor 56 and the outer conductor 54 can electrically isolate the inner and outer conductors from each other. In some implementations, the insulation 58 is formed of a compressible or readily movable material, such that damaging the cartridge 12 will likely cause the outer conductor 54 to come into contact with the inner conductor 56. In some implementations, the insulation layer 58 is an air gap. In some implementations contact is not necessary, and merely a change in spacing (or amount of insulation 58) between the inner conductor 56 and the outer conductor 54 is detectable by the testing circuit (shown in FIGS. 4A-4C) which can signify that the cartridge 12 has been damaged or breached. In some implementations, the insulation 58 is a plastic of fibrous mesh, in which the fibers will move in response to compressive force, such as the outer conductor 54 being punctured and pressed into the insulation 58. In some implementations, the insulation 58 is a foam, a fluid, or a coating applied to at least one of the conductors which inhibits conduction of electricity when the spacing between the inner conductor 56 and the outer conductor 54 has not been altered, but is displaced when the conductors are pressed together. In some implementations, the insulation layer 58 is a dielectric material that becomes electrically polarized in the presence of an electric field (e.g., if a voltage is applied across the inner conductor 56 and the outer conductor 54). In these implementations, the insulation 58 can increase a capacitance that exists between the inner and outer conductors, which can be useful in implementations where the testing circuit measures the capacitance of the conductive shell 50.

Figure 4A:
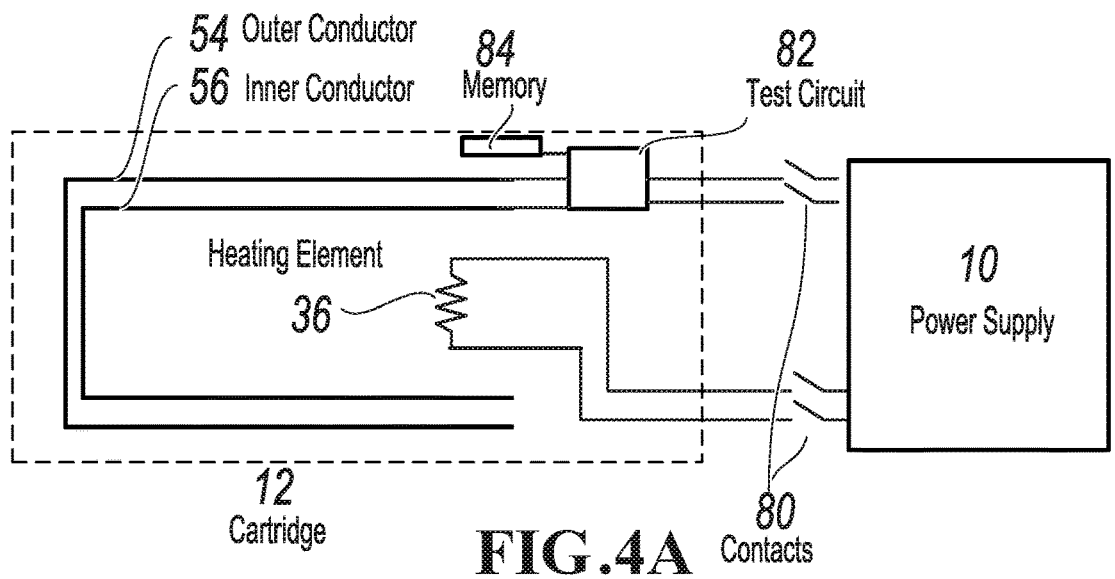
FIGS. 4A-4C depict example wiring diagrams for a personal vaporizer with a testing circuit.
Figure 4B:
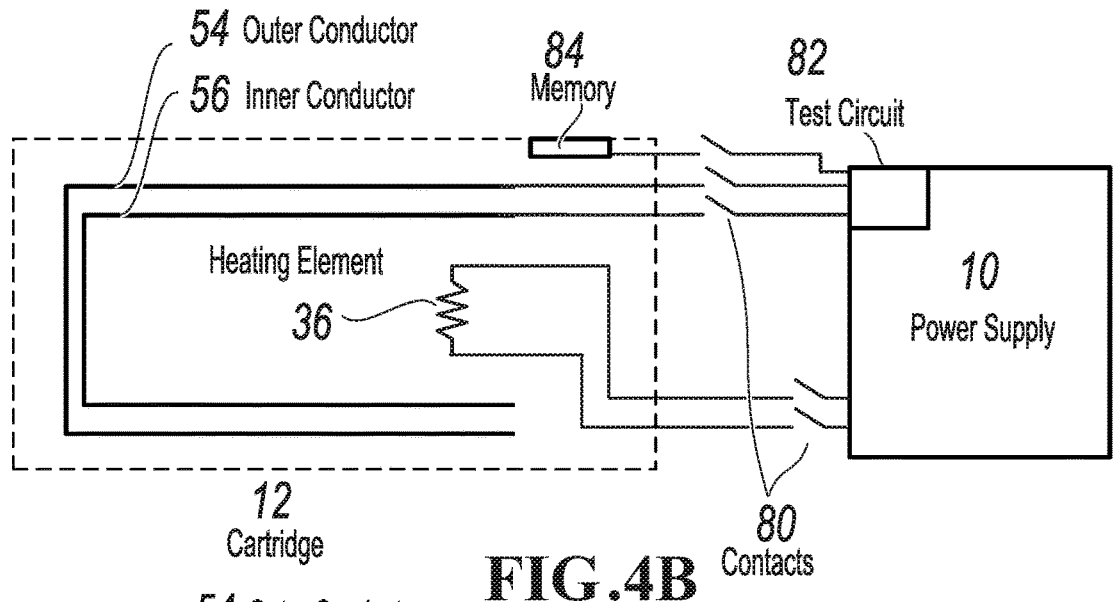
Figure 4C:
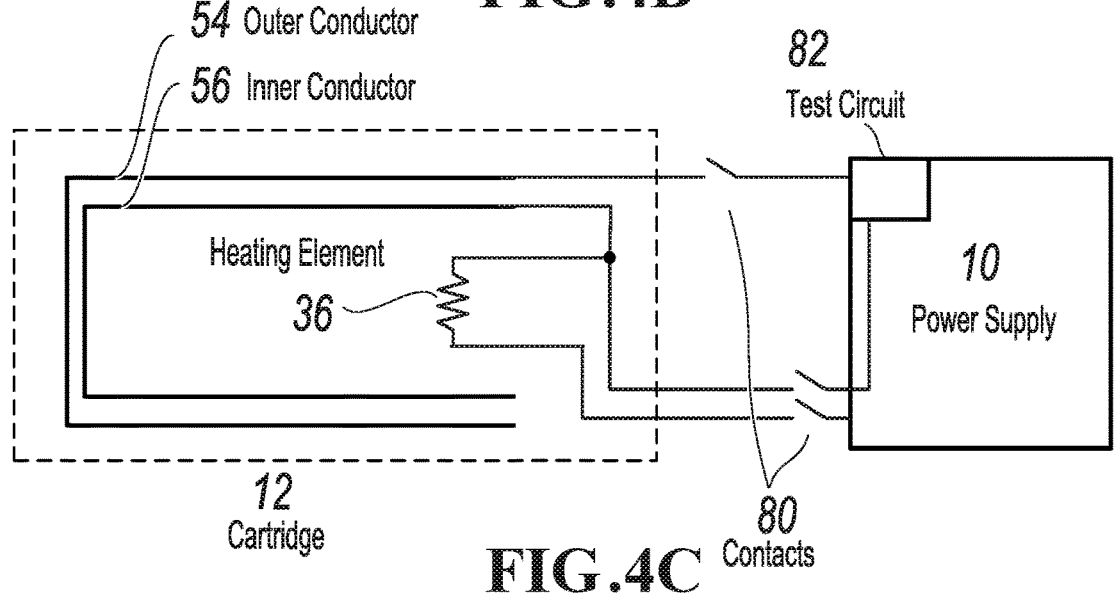

FIGS. 4A-4C depict example wiring diagrams for a personal vaporizer with a test circuit. Test circuit 82 can use the conductive shell 50 to assess whether or not the cartridge 12 has been breached or otherwise damaged. The test circuit 82 can be located within the cartridge 12 (as shown in FIG. 4A) or separate from the cartridge 12 but within the personal vaporizer (e.g., within the power supply portion 10 as shown in FIGS. 4B and 4C) or remote from the personal vaporizer (e.g., at a test bench in a manufacturing facility or quality control location). The test circuit 82 can be in electrical contact with both the inner conductor 56 and the outer conductor 54 of the conductive shell 50. For example, in implementations where the inner conductor is in electrical contact with the mechanical coupler 14, and where the mechanical coupler 14 includes a part on the cartridge 12 and a mating part on the power supply portion of a personal vaporizer, the test circuit 82 can have a contact in electrical contact such that a connection is made when the cartridge is coupled to the power supply portion of the personal vaporizer. Returning to FIG. 3, an additional connection can be made between the conductive tabs 60 and the test circuit 82, and the conductive tabs 60 can be in electrical connection with the outer conductor 54. In another example implementation, both the outer conductor 54 and the inner conductor 56 can be connected to one or more conductive tabs 60, which can be offset on the base of the cartridge 12 (e.g., rotated by 30 degrees). The testing circuit can then have two or more contacts which make connections with the conductive tabs 60 upon coupling the cartridge 12 with a power supply portion (or other system that includes the testing circuit).

The test circuit 82 as shown in FIGS. 4A-4C can assess the integrity of the conductive shell 50 by measuring one or more electrical parameters associated with the conductive shell 50. For example, the testing circuit can perform a continuity check between the inner conductor 56 and the outer conductor 54. In these examples, the testing circuit can apply a small voltage across the two conductors of the conductive shell 50 and determine whether or not current flows between them. In some instances, the testing circuit can measure a capacitance associated with the conductive shell 50. For example, the testing circuit can apply a series of alternating current (AC) signal voltages across the conductors. The testing circuit can use the series of AC signals to determine a resonant frequency, and thus a capacitance associated with the conductive shell 50. In instances where there is damage or deformations in the geometry between the inner conductor 56 and the outer conductor 54, the capacitance of the conductive shell 50 will be different than a nominal capacitance which can be determined, at the time of manufacture. In some implementations, a known or selected resistance exists between the two conductors of the conductive shell 50. The testing circuit can measure this resistance and assess that a breach has occurred if there is significant deviation from the expected resistance. Any combination of the foregoing testing methods are considered within the scope of this disclosure. For example, a conductive shell 50 can have a third conductor (not shown), intermediate the inner and outer conductors. The testing circuit can measure both a capacitance between the outer and inner conductors, and a resistance between the outer and third conductors.

In some implementations, test circuit 82 can be in communication with a memory 84. The memory 84 can store information related to the cartridge, such as a serial number, lot number, manufacturing location etc. Communication between memory 84 and test circuit 82 can be analog or digital and can be direct or indirect (e.g., pass through the power supply portion 10). In some implementations memory 84 can be re-writable, for example memory 84 can be EEPROM or flash memory, which allows the test circuit 82 to write to the memory 84. For example, if a cartridge fails a test, and thus has been penetrated or damaged, the test circuit 82 can write a flag to memory 84, which indicates the cartridge should not be used. In this example, if the cartridge 12 is removed and coupled with a different power supply 10, the new test circuit 82 could immediately identify the cartridge 12 as faulty, based on the flag present in memory 84. In some implementations, as shown in FIG. 4A the test circuit and memory can be entirely self-contained within the cartridge 12. In these implementations, the test circuit 82 can periodically test the cartridge 12 regardless of whether it is coupled with a power supply 10. In some implementations, the power supply 10 can receive a flag signal from memory 84 either as a result of a query, or pushed from memory 84 which indicates a status of the cartridge.

One or more contacts 80 can be provided between the power supply 10 and the cartridge 12 of the personal vaporizer. The contacts 80 can be reinforced conductive material, such as conductive tabs 60 depicted in FIG. 3, or conductive components of the cartridge 12 itself, such as threats of the mechanical coupler, or an external wall of the cartridge 12. The contacts 80 can be configured to form an electrical connection when the cartridge 12 is coupled with the power supply 10. In some implementations, contacts 80 can be electronically controlled (e.g., using field effect transistors). In these implementations, the test circuit 82 can open or shut some or all of the contacts as necessary to operate. For example, upon the cartridge 12 being coupled with the power supply 10, the test circuit 82 can perform a continuity check between the inner conductor 56, and outer conductor 54. If continuity exists, it can be determined that the conductive shell 50 has been breached, and the test circuit 82 can transmit a signal which opens contacts 80 and prevents power from being applied to the heating element 36.

FIG. 4C illustrates a wiring diagram of an example implementation which only requires three contacts 80. In this implementation, the inner conductor 56 is wired to a reference voltage (e.g., ground) that is shared with the heating element 36. As shown in FIG. 4C, only three contacts between the cartridge 12 and the power supply 10 are used, a ground or reference contact, a contact for delivering power to the heating element 36, and a contact for testing the outer conductor 54.

In some implementations, if the testing circuit assesses the integrity of conductive shell 50 is compromised, the personal vaporizer can take a specified action. For example, the personal vaporizer (e.g., personal vaporizer 2 as described with reference to FIG. 1) can shut down, or electrically disconnect the heating element, preventing the cartridge 12 from being used. In some implementations, in response to a failed integrity test from the testing circuit, the cartridge 12 can be rendered inoperable or otherwise permanently damaged. For example, a large surge of electricity can be supplied to the heating element, causing it to break and preventing further use. In some implementations, an indication can be provided of a failed test. For example, an LED or audible warning can be provided, letting the user know that the cartridge 12 has been damaged or altered.

In some implementations, additional breach responsive devices are included in the cartridge 12. For example, reservoir 38 can be partitioned by a frangible wall (not shown) which will break in response to tampering and cause a secondary substance stored within the partition to mix with a primary substance to be atomized. The mixing of the secondary and primary substances can render the cartridge unusable, or otherwise undesirable. In example of a frangible wall system with a secondary substance, suitable for use with the cartridge 12, is described in U.S. application Ser. No. 16/987,037, entitled "PERSONAL VAPORIZER CARTRIDGE WITH TAMPER RESPONSIVE RESERVOIR," filed Aug. 6, 2020.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

The invention claimed is:

1. A personal vaporizer cartridge, comprising:
   a housing comprising a shell and a base, wherein the housing is configured to couple with a power supply portion of a personal vaporizer, and wherein the shell comprises:
      a first conductive layer;
      a second conductive layer; and
      an insulation layer between the first and second conductive layers, electrically isolating the first conductive layer from the second conductive layer, wherein the first and second conductive layers are configured to be connected a testing circuit, wherein the testing circuit measures at least one electrical parameter associated with the shell;
   a reservoir enclosed by the housing, and configured to contain a substance to be vaporized; and
   a wick configured to transport the substance from the reservoir to an atomization chamber.

2. The cartridge of claim 1, wherein the atomization chamber is configured to atomize the substance to be vaporized and generate an aerosol, the atomization chamber comprising:
   a heating element; and
   an air inlet to allow airflow through the atomization chamber into a chimney, wherein the chimney forms a channel between the atomization chamber and an external space.

3. The cartridge of claim 1, wherein the insulation layer is a dielectric material, and wherein a predetermined capacitance is present between the first conductive layer and the second conductive layer.

4. The cartridge of claim 3, wherein the testing circuit is configured to:
   measure a capacitance between the first conductive layer and the second conductive layer; and
   compare the measured capacitance with the predetermined capacitance.

5. The cartridge of claim 1, wherein the first conductive layer is electrically connected to a voltage reference on the cartridge, and the second conductive layer further comprises a conductive tab that penetrates the base, and is configured to form an electric connection with the testing circuit on the power supply portion of the personal vaporizer.

6. The cartridge of claim 1, wherein an outer surface of the second conductive layer is enclosed with a paper, plastic, or printed material.

7. The cartridge of claim 1, wherein the electrical parameter associated with the shell is a continuity between the first conductive layer and the second conductive layer.

8. A method for assessing the condition of a cartridge of a personal vaporizer, the method comprising:
   upon the cartridge being coupled with a power supply portion of the personal vaporizer, analyzing an electrical characteristic between a first conductive layer and second conductive layer of a shell which encloses at least a portion of a fluid reservoir of the cartridge, wherein the cartridge comprises an insulation layer between the first and second conductive layers, electrically isolating the first conductive layer from the second conductive layer; and
   in response to analyzing the electrical characteristic, determining that the shell has been breached.

9. The method of claim 8, wherein analyzing the electrical characteristic comprises performing a continuity check, and wherein it is determined the shell has been breached when there is continuity between the first conductive layer and the second conductive layer.

10. The method of claim 8, wherein analyzing the electrical characteristic comprises measuring a capacitance, and wherein it is determined that the shell has been breached when the capacitance is below a predetermined threshold.

11. The method of claim 8, further comprising:
    in response to determining the cartridge has been breached performing an action.

12. The method of claim 11, wherein the action includes interrupting a signal between the power supply portion of the personal vaporizer and a heating element.

13. The method of claim 11, wherein the action includes electrically overloading at least one component in the cartridge.

14. The method of claim 11, wherein the action includes providing an indication that the cartridge has been breached.

15. A personal vaporizer configured to atomize a substance and generate an aerosol, the vaporizer comprising:
    a power supply portion comprising a battery;
    a cartridge portion, configured to be coupled to the power supply portion and comprising a shell, wherein the shell comprises:
       a first conductive layer;
       a second conductive layer; and
       an insulation layer between the first and second conductive layers, electrically isolating the first conductive layer from the second conductive layer;
    a testing circuit, configured to measure at least one electrical parameter associated with the shell.

16. The personal vaporizer of claim 15, wherein the testing circuit is within the power supply portion.

17. The personal vaporizer of claim 16, wherein the first conductive layer is electrically connected to a voltage reference on the cartridge, and the second conductive layer further comprises a conductive tab that penetrates a base of the cartridge, and is configured to form an electric connection with the testing circuit on the power supply portion of the personal vaporizer.

18. The personal vaporizer of claim 15, wherein the testing circuit is within the cartridge portion.

19. The personal vaporizer of claim 15, wherein the electrical parameter associated with the shell comprises at least one of electrical continuity;
   a capacitance between the first conductive layer and the second conductive layer; or
   a resistance between the first conductive layer and the second conductive layer.

20. The personal vaporizer of claim 15, wherein an outer surface of the second conductive layer is enclosed with a paper, plastic, or printed material.

* * * * *